United States Patent [19]
Engle et al.

[11] Patent Number: 5,482,033
[45] Date of Patent: Jan. 9, 1996

[54] ANESTHETIC WASTE GAS EVACUATION SYSTEM

[76] Inventors: John R. Engle, 103 Duncan Ave., Paris, Ky. 40361; Jeff Baker, 185 Forest Park, Lexington, Ky. 40502

[21] Appl. No.: 192,362

[22] Filed: Feb. 8, 1994

[51] Int. Cl.[6] .............................. A62B 31/00; A62B 9/02
[52] U.S. Cl. .............. 128/205.19; 128/910; 128/205.24
[58] Field of Search ................. 128/203.12, 204.18, 128/205.11, 205.12, 205.13, 205.19, 205.24, 909, 910; 454/341, 49; 55/410, 467

[56] References Cited

U.S. PATENT DOCUMENTS

| | | | |
|---|---|---|---|
| 3,229,896 | 1/1966 | Levy | 454/341 |
| 3,505,989 | 4/1970 | Truhan | 128/205.26 |
| 3,721,239 | 3/1973 | Myers | 128/205.12 |
| 4,176,666 | 12/1979 | Hovey | 128/910 |
| 4,312,339 | 1/1982 | Thompson, Sr. | 128/910 |
| 4,527,558 | 7/1985 | Hoenig | 128/205.24 |
| 4,538,605 | 9/1985 | Gedeon et al. | 128/910 |
| 4,838,257 | 6/1989 | Hatch | 128/204.18 |
| 4,840,169 | 6/1989 | Folsom | 128/910 |
| 4,945,906 | 8/1990 | Lindkvist | 128/910 |
| 4,987,894 | 1/1991 | Kight | 454/49 |
| 5,033,464 | 7/1991 | Pleastilho | 128/910 |
| 5,345,928 | 9/1994 | Lindkvist | 128/205.12 |

*Primary Examiner*—Edgar S. Burr
*Assistant Examiner*—V. Srivastava
*Attorney, Agent, or Firm*—Harness, Dickey & Pierce

[57] ABSTRACT

An anesthesia waste gas evacuation system having a waste gas collection chamber with an inlet into the chamber at the bottom and a blower at the top for blowing gas from the chamber to an outlet connected to a building ventilation system. Vents are provided to provide communication between the chamber interior and the surrounding atmosphere so that the pressure within the chamber remains substantially at atmospheric pressure avoiding the formation of a sub-ambient pressure within the chamber. The chamber is electrically grounded and is electrically connected to a standpost so as to ground the post as well.

10 Claims, 1 Drawing Sheet

ANESTHETIC WASTE GAS EVACUATION SYSTEM

BACKGROUND AND SUMMARY OF THE INVENTION

The present invention relates to an anesthetic waste gas evacuation system and in particular an evacuation system for removing anesthetic gases discharged from an anesthesia machine without exposing the patient to a subambient pressure or a state of positive end expiratory pressure.

During normal operation of an anesthesia machine, either in a rebreathing or a non-rebreathing mode, a quantity of the anesthetic gas will be discharged from the machine as waste gas. It is essential that this gas be properly evacuated from the room in which it is being used to the outside ambient atmosphere. It is essential in an evacuation system that there be no vacuum produced at the discharge valve of the anesthesia machine that can interfere with the breathing of the patient.

The evacuation system of the present invention avoids either a subambient pressure or a state of positive end expiratory pressure. This is accomplished by providing a gas collection chamber with the waste gas being introduced into the bottom of the chamber and a small turbine fan at the top of the chamber draws the waste gas and actively pushes the waste gas into an outlet conduit. To avoid a subambient or a state of positive end expiratory pressure within the collection chamber, one or more vents are formed in the collection chamber to provide communication between the chamber and the ambient atmosphere. The net effect of the vents is that the pressure within the chamber will be equal to or very close to the ambient pressure. By allowing the heavier than air waste gas to collect at the bottom of the chamber and drawing this waste gas out through a fan at the top, there is little or no effect on the expiration of the patient.

The gas collection chamber is formed by a metallic housing which is grounded through the electrical power cord. The housing is coupled to a mounting post through an electrically conductive bracket so that the post is also grounded. All other components mounted to the post can be easily grounded by appropriate connection to the post.

Further objects, features and advantages of the invention will become apparent from a consideration of the following description and the appended claims when taken in connection with the accompanying drawings.

DETAILED DESCRIPTION OF THE PREFERRED EMBODIMENT

Figure 1:
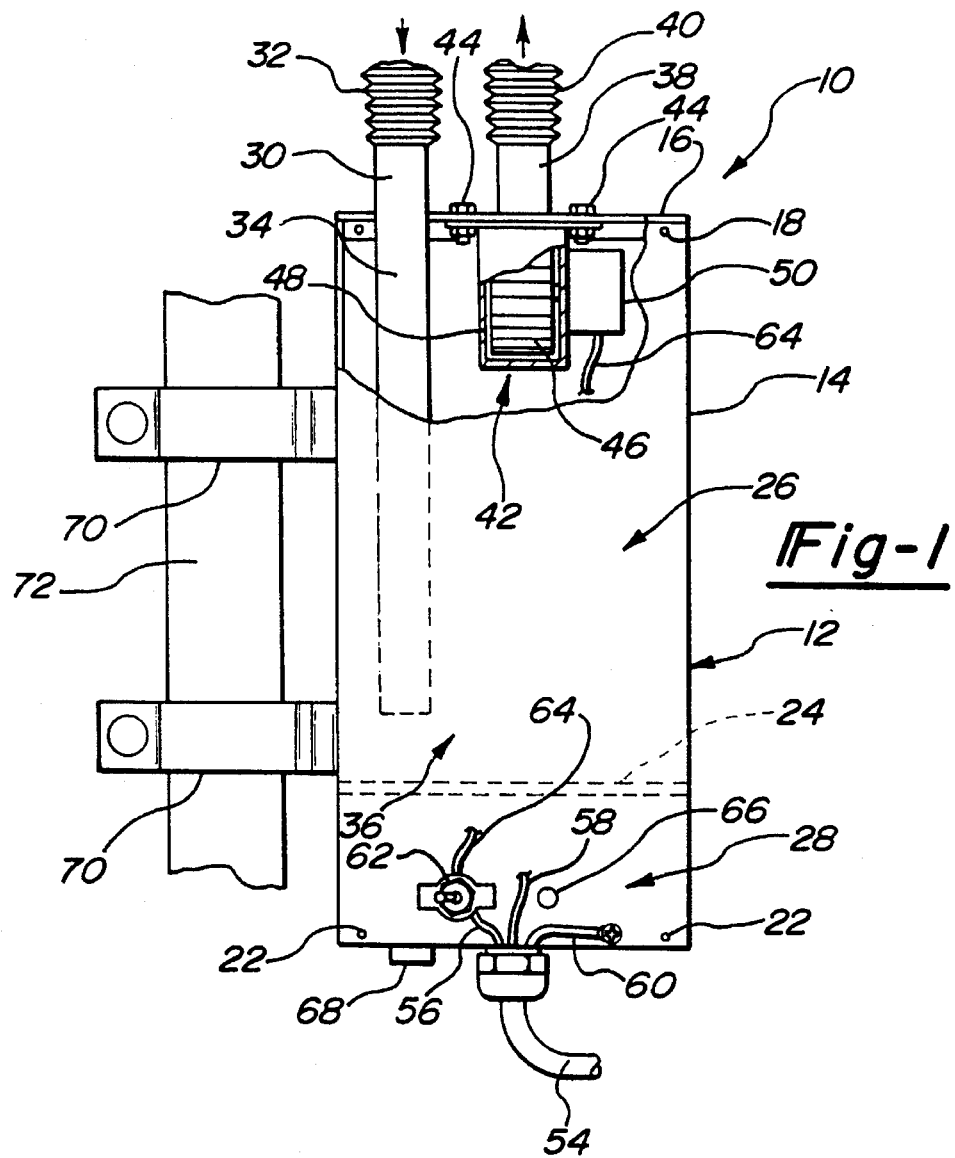
FIG. 1 is a side view of the evacuation system of the anesthetic waste gas evacuation system of the present invention.
Figure 2:
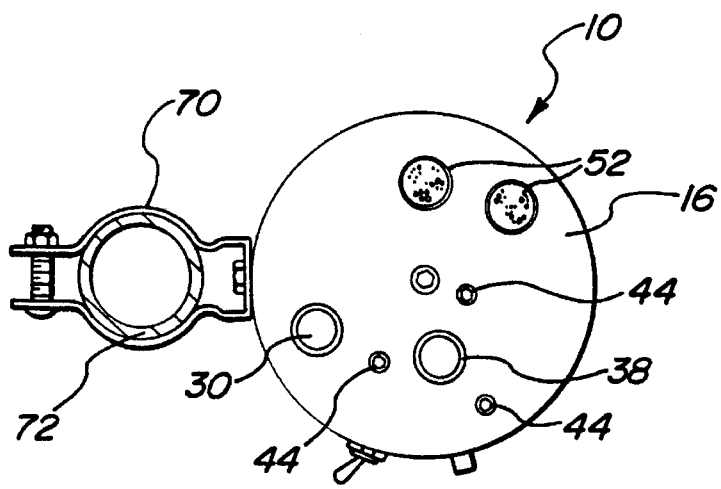
FIG. 2 is a top view of the anesthetic waste gas evacuation system of the present invention.

The anesthetic waste gas system of the present invention is shown in FIG. 1 and designated generally at 10. System 10 is comprised principally of a housing 12 which is constructed of a cylindrical canister 14 having a top plate 16 and a bottom plate 20. The top and bottom plates are attached by screws 18 and 22 respectively. An intermediate wall 24 within the canister 14 divides the canister into an upper gas collection chamber 26 and a lower electronics chamber 28. The intermediate wall 24 is sealed to the canister 14 to prevent gas in the chamber 26 from passing into the electronics chamber 28.

The top plate 16 has a gas inlet connection 30 formed integrally with the top plate. The gas inlet connection is a standard size fitting for connection to one end of a conduit 32, the other end of which is connected to the discharge valve or pop-off valve of an associated anesthesia machine (not shown). The conduit 32 directs the discharged anesthetic waste gas from the anesthesia machine to the gas collection chamber 26. A stand pipe or tube 34 within the gas collection chamber directs the waste gas from the inlet connection 30 to a lower portion 36 of the gas collection chamber 26. The housing 12 is placed below the pop-off valve of the anesthesia machine so that the waste gas, which is heavier than air, can passively settle through the conduit 32 and stand pipe 34 into the bottom of the chamber 26. The pipe 34 can be omitted if the inlet gas connection 30 is positioned at the lower end of the chamber rather than in the top plate 16. The top plate 16 provides a convenient location for the inlet 30 since the top plate is flat thus enabling the inlet to be easily formed integral with the top plate in a leak proof manner.

A gas outlet connection 38 is also integrally formed in the top plate 16. The outlet connection 38 is also a standard fitting for connection with a conduit 40 which directs gases discharged from the chamber 26 to a building vent for removal from the building in which the anesthesia machine is being used. Once discharged into the atmosphere, the anesthetic agent will be quickly diluted to a harmless concentration. A small blower 42 is disposed within the chamber 26 and is mounted to the top plate 16 by a plurality of nut and bolt fastener assemblies 44. The blower 42 is coupled to the outlet connection 38 and includes a turbine fan 46 for blowing gas from the chamber 26 into the outlet conduit 40. The blower 42 has a gas inlet 48 along one side for receiving gas from the collection chamber 26. An electric motor 50 is coupled to the blower 42 for turning the fan 46. By operating the blower 42, gases collected in the chamber 26 are forced into the outlet conduit. The chamber 26 is large enough to collect the entire tidal volume of the patent to which it is attached by means of the anesthesia machine.

The top plate 16 is provided with one or more vents 52 which provide communication through the top plate 16 between the ambient atmosphere surrounding the housing 12 and the interior of the chamber 26. As a consequence, as the blower 42 is operated and gas is discharged through the conduit 40, atmospheric air will be drawn through the vents into the chamber so that the internal pressure within the chamber remains equal to or close to the ambient atmospheric pressure. As a result, there is no vacuum in the inlet conduit 32 that is connected to the discharge or pop-off valve of the anesthesia machine. Accordingly, there is no need for a vacuum regulator in the conduit 32. With the absence of a vacuum or subambient pressure within the conduit 32 there can be no subambient condition experienced by the patient. Furthermore, since the pressure within the chamber 26 can not exceed the atmospheric pressure by virtue of the vents 52, there will not be a state of positive end expiration pressure within the collection chamber 26 as well. This provides a safe environment for the patient while also ensuring that the waste gases are properly evacuated. The fan is sized and operated at a speed to discharge air at approximately three times the respiration flow of the patient. The vents at the top of the chamber, which are closer to the blower than the bottom of stand pipe 34, ensure that outside air is drawn into the chamber to supply the fan.

A power cord 54 is coupled to the bottom plate 20 of the housing and includes a pair of electrical power wires 56 and 58 and a ground wire 60. The power wire 56 is connected in a circuit with a switch 62 and the motor 50 through the wire 64. The electrical circuit includes an on/off indicator light 66 and a fuse (not shown) mounted by the fuse holder 68 in the bottom plate 20.

The ground wire 60 is connected to the bottom plate 20 for grounding of the housing 12. The housing 12 has a pair of mounting brackets 70 connected thereto for mounting the housing to a mounting post 72 conventionally used for the anesthesia machine. At least one of the brackets 70 is electrically conductive so that the mounting post 72 is also grounded through the ground wire 60. Any other components attached to the mounting post can thus be easily grounded by electrically connecting the components to the post.

The waste gas evacuation system of the present invention provides a convenient and easy to use system which ensures that the patient is not exposed to a subambient or a positive end expiratory pressure condition. This is accomplished by maintaining the gas collection chamber at atmospheric pressure while actively blowing the gases from within the chamber to a building vent.

It is to be understood that the invention is not limited to the exact construction illustrated and described above, but that various changes and modifications may be made without departing from the spirit and scope of the invention as defined in the following claims.

I claim:

1. An anesthetic waste gas evacuation system for use with an anesthetic machine delivering an anesthetic gas to a patient, the machine having a discharge valve for discharging anesthetic waste gas, said system comprising:

a housing forming a gas collection chamber having upper and lower spaced ends;

a gas inlet for introducing gas into said gas collection chamber adjacent said lower end;

inlet conduit means coupled to said inlet for directing anesthetic waste gas to said inlet;

a gas outlet adjacent said upper end of said gas collection chamber;

blower means having a gas inlet in communication with said gas collection chamber for receiving anesthetic waste gas from said gas collection chamber;

outlet conduit means in communication with said blower means for receiving anesthetic waste gas from said blower means; and vent means in said housing at said upper end of said gas collection chamber for providing vapor communication between the interior of said gas collection chamber and the ambient atmosphere whereby the air pressure within said gas collection chamber remains approximately at atmospheric pressure.

2. The anesthetic waste gas evacuation system of claim 1 wherein said chamber has a top wall with said vent means being disposed in said top wall and said blower means being mounted to said top wall within said chamber whereby the anesthetic waste gas received in said gas collection chamber at said lower end is drawn into the blower means before escaping from said gas collection chamber through said vent means.

3. The anesthetic waste gas evacuation system of claim 1 wherein said chamber has a volume at least as large as the tidal volume of the patient.

4. The anesthetic waste gas evacuation system of claim 1 wherein said blower means has an output capacity to discharge air at approximately three times the respiration flow of the patient.

5. The anesthetic waste gas evacuation system of claim 1 wherein said blower means includes a fan and an electric motor for rotating said fan, said evacuation system further comprising an electric power cord attached to said housing for supplying electric power, and circuit means for connecting said power cord to said motor, said circuit means including switch means for selectively turning said motor on and off.

6. The anesthetic waste gas evacuation system of claim 5 wherein said housing is electrically conductive and said power cord includes a ground wire connected to said housing to ground said housing; and said system further comprising electrically conductive bracket means for attaching said housing to a mounting pole whereby said pole is electrically grounded through said bracket means.

7. The anesthetic waste gas evacuation system of claim 1 further comprising means for electrically grounding said housing.

8. The anesthetic waste gas evacuation system of claim 7 further comprising attaching means for attaching said housing to a vertical stand post and for grounding said post through said attaching means.

9. The anesthetic waste gas evacuation system of claim 1 wherein said gas inlet includes a inlet fitting at the upper end of said chamber for coupling said inlet conduit to said chamber and a tube extending downward from said fitting to said lower end of said gas collection chamber whereby the anesthetic waste gas flows downward through said tube into said gas collection chamber at said lower end.

10. The anesthetic waste gas evacuation system of claim 9 wherein said gas collection chamber has a top wall and said inlet fitting is disposed in said top wall and said tube extends downward from said top wall to said lower end.

\* \* \* \* \*